United States Patent
Coimbra et al.

(10) Patent No.: US 7,015,180 B2
(45) Date of Patent: Mar. 21, 2006

(54) HAIR TREATMENT COMPOSITIONS COMPRISING AN ANIONIC SURFACTANT AND A C8-C22 ALKYL DIMETHYL HYDROXYETHYL AMMONIUM CHLORIDE

(75) Inventors: Luiz Fernando Coimbra, Sao Paulo (BR); Manlio Gallotti, Sao Paulo (BR); Simone Bergamo Quartarolli, Sao Paulo (BR)

(73) Assignee: Clariant S.A., Sao Paulo-SP (BR)

( * ) Notice: Subject to any disclaimer, the term of this patent is extended or adjusted under 35 U.S.C. 154(b) by 50 days.

(21) Appl. No.: 10/220,462

(22) PCT Filed: Feb. 23, 2001

(86) PCT No.: PCT/BR01/00022

§ 371 (c)(1),
(2), (4) Date: Dec. 9, 2002

(87) PCT Pub. No.: WO01/64180

PCT Pub. Date: Sep. 7, 2001

(65) Prior Publication Data
US 2003/0148902 A1    Aug. 7, 2003

(30) Foreign Application Priority Data
Feb. 29, 2000 (BR) .................... 0001261
Sep. 21, 2000 (EP) .................... 00120643

(51) Int. Cl.
*C11D 1/65* (2006.01)

(52) U.S. Cl. ............... 510/127; 510/119; 510/123; 510/426; 510/427; 510/504

(58) Field of Classification Search ........... 510/127, 510/119, 123, 426, 427, 504
See application file for complete search history.

(56) References Cited

U.S. PATENT DOCUMENTS

| | | | | |
|---|---|---|---|---|
| 4,165,367 A | * | 8/1979 | Chakrabarti | 424/47 |
| 4,235,759 A | * | 11/1980 | Ohbu et al. | 510/427 |
| 4,411,884 A | * | 10/1983 | Jacquet et al. | 424/47 |
| 4,744,977 A | * | 5/1988 | Hensen et al. | 424/70.19 |
| 4,919,839 A |   | 4/1990 | Durbut et al. | |
| 5,145,607 A | * | 9/1992 | Rich | 510/122 |
| 5,294,230 A | * | 3/1994 | Wu et al. | 8/127.51 |
| 5,512,699 A | * | 4/1996 | Connor et al. | 564/153 |
| 5,629,278 A | * | 5/1997 | Baeck et al. | 510/236 |
| 5,679,630 A | * | 10/1997 | Baeck et al. | 510/305 |
| 5,714,446 A | * | 2/1998 | Bartz et al. | 510/119 |
| 5,997,854 A | * | 12/1999 | von Mallek | 424/70.19 |
| 6,015,784 A | * | 1/2000 | Kazuta et al. | 510/446 |
| 6,444,628 B1 | * | 9/2002 | Nocerino et al. | 510/124 |

FOREIGN PATENT DOCUMENTS

| | | |
|---|---|---|
| EP | 0395332 | 10/1990 |
| EP | 0384715 B1 | 9/1995 |
| GB | 1295108 | 11/1972 |
| GB | 2292155 A | 2/1996 |
| WO | WO 98/23720 | 6/1998 |
| WO | WO 98/59024 | 12/1998 |
| WO | WO 99/43773 | 9/1999 |

OTHER PUBLICATIONS

International Search Report, Jul. 23, 2001.
Liquid Fabric Softeners; Clariant Functional Chemicals—Markets, May 8, 2000.
Karl Heinz Schrader, "Grundlagen und Rezeptur der Kosmetika", 1989.

* cited by examiner

*Primary Examiner*—Charles Boyer
(74) *Attorney, Agent, or Firm*—Richard P. Silverman

(57) ABSTRACT

The inventions relates to stable cosmetic compositions preferably hair treatment compositions, comprising
a) from 0,1% to 70% by weight of at least one anionic surfactant
b) from 0,05% to 10% by weight of at least one cationic surfactant of the formula (1)

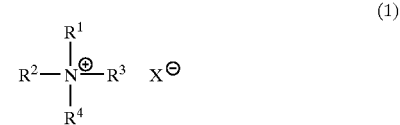

(1)

Wherein
$R^1$ is selected from the group consisting of $(C_8-C_{22})$-alkyl, $(C_8-C_{22})$-alkenyl, $(C_8-C_{22})$-alkylamidopropyl, $(C_8-C_{22})$-alkenylamidopropyl, $(C_8-C_{22})$-alkoxypropyl and $(C_8-C_{22})$-alkenyloxypropyl,
$R^2$, $R^3$ and $R^4$ are the same or different and are independently from each other selected from the group consisting of $(C_1-C_{22})$-alkyl, $(C_1-C_{22})$-alkenyl and groups having the formula —A—$(AO)_n$—OH, wherein A is $C_2H_4$ and/or $C_3H_6$, n is a number from 0 to 20, with the provision that at least one the radicals $R^2$, $R^3$ and $R^4$ is a group having said formula —A—$(AO)_n$—OH, and X is an anionic; and
c) optionally from 0.1% to 15% by weight of one or more amphoteric and/or nonionic surfactants.

8 Claims, No Drawings

HAIR TREATMENT COMPOSITIONS COMPRISING AN ANIONIC SURFACTANT AND A C8-C22 ALKYL DIMETHYL HYDROXYETHYL AMMONIUM CHLORIDE

The present invention relates to cosmetic compositions, preferably hair treatment compositions, comprising anionic and cationic surfactants.

Cosmetic compositions comprising anionic and cationic surfactants, i.e. surfactants which are considered to be non-compatible under normal conditions, often show low stability during storage because of precipitation and/or phase separation.

Shampoo compositions comprising particular surfactant systems have already been developed in order to provide improved results of stability and combing performance. U.S. Pat. No. 5,714,446, for example, refers to a shampoo composition comprising, as essential component, a nonionic silicone hair conditioning agent. According to that document, the improved cleaning and conditioning results are obtained by using an anionic detersive surfactant together with a nonionic and insoluble silicone compound and a critically selected cationic surfactant. It teaches that the cationic surfactants provide enhanced hair combing for permed or damage hair when combined with the cationic surfactant having nonionic hydrophilic moieties. Moreover, it teaches that the anionic surfactant is used just for enhanced cleaning purposes and therefore, the improvements obtained by compositions described in U.S. Pat. No. 5,714,446 deals with the interaction between the cationic and the silicone surfactants.

Document GB 1,295,108 refers to a single phase shampoo composition for improving the combing properties which essentially comprises a non-volatile oil together with anionic, cationic and amphoteric surfactants, wherein said oil could not be used in concentrations higher than 5% by weight without affecting the stability of the composition (phase separation). Therefore, the composition defined in GB 1,295,108 still fails in providing the desired stability properties Applicants have now discovered that cosmetic compositions comprising at least one adduct formed by at least one anionic surfactant and at least one cationic surfactant of the formula (1) are stable during storage.

According to the present invention there are provided cosmetic compositions comprising a) from 0,1% to 70% by weight of at least one anionic surfactant b) from 0,05% to 10% by weight of at least one cationic surfactant of the formula (1)

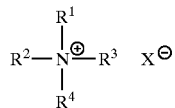

(1)

wherein $R^1$ is selected from the group consisting of $(C_8-C_{22})$-alkyl, $(C_8-C_{22})$-alkenyl, $(C_8-C_{22})$alkylamidopropyl, $(C_8-C_{22})$-alkenylamidopropyl, $(C_8-C_{22})$-alkoxy-propyl or $(C_8-C_{22})$-alkenyloxypropyl $R^2$, $R^3$ and $R^4$ are the same or different and are independently from each other selected from the group consisting of $(C_1-C_{22})$-alkyl, preferably $(C_1-C_4)$-alkyl, highly preferred $CH_3$ $(C_1-C_{22})$-alkenyl, preferably $(C_1-C_4)$-alkenyl, and groups having the formula —A—$(OA)_n$—OH, wherein A is $C_2H_4$ and/or $C_3H_6$, preferably $C_2H_4$ and n is a number from 0 to 20, preferably 0 to 5, highly preferred 0, with the provision that at least one of the radicals $R^2$, $R^3$ and $R^4$ is a group having said formula —A—$(AO)_n$—OH, and $X^-$ is an a anion, preferable chloride, bromide, sulphate or methosulphate, highly preferred chloride; and c) optionally from 0.1% to 15% by weight of one or more nonionic and/or amphoteric surfactants.

Preferably the present compositions comprise from 2 to 50%, highly preferred from 2 to 10% by weight, of anionic surfactants a) from 0.5 % to 8.0% highly preferred from 0.5% to 2.5% by weight, of cationic surfactants b) of formula (1) and from 0.1 to 5% by weight of nonionic and/or amphoteric surfactants c)

Preferred cationic surfactants according to formula (1) are such wherein $R^2$, $R^3$ and $R^4$ are the same or different and are independently from each other selected from the group consisting of $CH_3$ and groups of the formula —A—$(OA)_n$—OH, wherein A is $C_2H_4$ and/or $C_3H_6$, preferably $C_2H_4$, n is a number from 0 to 20, preferably 0 to 5, highly preferred 0, with the provision that at least one of radicals $R^2$, $R^3$ and $R^4$ is a group having said formula —A—$(AO)_n$—OH.

Highly preferred as cationic surfactant of the formula (1) is alkyl dimethyl-hydroxyethyl ammonium chloride.

Preferred anionic surfactants are selected from the group consisting of alkyl sulfates, alkyl ether sulfates, secondary alkane sulfonates, alpha olefin sulfonates, acyl isocyanates, linear alkylbenzene sulfonates, isethionates, and mixtures thereof.

Said alkyl ether sulfates are preferably water-soluble salts or acids of the formula $RO(A)_mSO_3M$, wherein R is an unsubstituted $(C_{10}-C_{24})$-alkyl or $(C_{10}-C_{24})$-hydroxyalkyl radical, preferably a $(C_{12}-C_{20})$-alkyl or $(C_{12}-C_{20})$-hydroxyalkyl radical, particularly preferred a $(C_{12}-C_{18})$-alkyl or a $(C_{12}-C_{18})$-hydroxyalkyl radical; A is an ethoxy or propoxy unit; m is a number greater than 0, preferably between 0.5 and 6, particularly preferred between 0.5 and 3; and M is a hydrogen atom or a cation, preferably a metal cation like sodium, potassium, lithium, calcium or magnesium, an ammonium cation a substituted ammonium cation, preferably a methylammonium, di-methylammonium, trimethylammonium, mono-, di- or triethanolammonium cation, or a quaternary ammonium cation, preferably a tetramethylammonium cation, a dimethylpiperidinium cation or a cation derived from alkylamines like ethylamine, diethylamine, triethylamine.

Particularly preferred alkyl ether sulfates are $(C_{12}-C_{18})$-alkyl-polyethoxylate (1.0) sulfate, $(C_{12}-C_{18})$-alkyl polyethoxylate (2.25) sulfate, $(C_{12}-C_{18})$-alkyl polyethoxylate (3.0) sulfate and $(C_{12}-C_{18})$-alkyl polyethoxylate (4.0) sulfate Said secondary alkane sulfonates can contain a saturated or unsaturated, alkyl group which can be linear or branched and which can optionally be substituted with a hydroxyl group. The sulfo group can be randomly distributed over the entire carbon chain.

Preferred secondary alkane sulfonates contain linear alkyl chains having from 9 to 25 carbon atoms, preferably from 10 to 20 carbon atoms, particularly preferred from 13 to 17 carbon atoms. Preferred cations are sodium, potassium, ammonium, mono-, di- or triethanolammonium, calcium, magnesium or mixtures thereof. Particularly preferred is sodium.

Said olefin sulphonates preferably contain linear or branched $(C_8-C_{22})$-alkyl or ($C_8$–$C_{22}$)-alkenyl groups. Preferred cations are sodium, potassium, ammonium, TEA, DEA, MEA, Triethylamine; magnesium, or mixtures thereof.

Said alkylbenzene sulfonates preferably contain linear alkyl chains having from 9 to 25 carbon atoms, preferably from 10 to 13 carbon atoms. The alkyl group can either be saturated or unsaturated and can be branched or linear. Optionally the alkyl group can be substituted by a hydroxyl group. Preferred cations are sodium, potassium, ammonium, mono-, di- or triethanolammonium, calcium or magnesium and mixtures thereof.

Said nonionic and amphoteric surfactants are preferably selected from the group consisting of alkyl polyalkylene glycols, alkylaryl polyalkylene glycols, alkyldimethyl amine oxides, dialkyl methyl amine oxides, alkylamidopropyl amine oxides, alkyl glucamides, alkyl polyglycosides, oxalkylated fatty acids, oxalkylated fatty acid esters, alkyl amines, alkyl amidopropyl betaines, alkyl dimethyl betaines and alkyl amphoacetates or -diacetates. The alkyl groups may be partially or fully replaced by alkenyl groups and may be linear or branched. Said alkyl groups preferably contain 8 to 22 carbon atoms. The polyalkylene glycol groups preferably contain 1 to 20 ethoxy and/or propoxy units.

Highly preferred amphoteric surfactants are cocamidopropyl betaine, sodium lauroamphoacetate and disodium lauroamphodiacetate.

Suitable co-surfactants are e.g. acyl glutamates, amide ether sulfates, methyl taurides, sarcosynates, Sodium Laureth 13-Carboxylate or mixtures thereof.

The compositions according to the present invention can optionally contain oils, emulsifiers, thickeners, natural and synthetic polymers, stabilizers, waxes, fillers, acids, bases, buffers, biological active compounds, vitamines, natural extracts, solubilizers, UV-absorber, perfumes, perfume carriers, pearlescing agents, dyes, bleaching agents and/or other ingredients conventionally used in cosmetic compositions.

The cosmetic compositions can be used widely in personal hygiene. Said compositions can be liquids, emulsions, lotions, creams, gels, or solids. If solids they are preferably used in the form of bars. Advantageously the rheology of said compositions can be adjusted over a wide range by varying the weight rations of said anionic and cationic surfactants.

Preferably the cosmetic compositions are hair treatment compositions like shampoos, lotions, creams, sprays and lacquers, preferably shampoos, highly preferred shampoos for african-ethnic hair.

Advantageously such hair treatment compositions provide an improved ability to comb the hair. Moreover they allow to reduce or even to eliminate emollient agents and conditioners like silicones, propyleneglycols and esters. When applied to african-ethnic hair such hair treatment compositions advantageously provide a positive hair volume decrease.

The invention is illustrated in the following non limiting examples, in which all percentages are on a weight basis unless otherwise.

EXAMPLE 1

Shampoo Formulation

| | |
|---|---|
| Sodium Lauryl Ether Sulfate (*Genapol LRO) | 7.85 |
| Alkyl Dimethyl Hydroxy Ethyl Ammonium Chloride (*Praepagen HY) | 0.98 |
| Sodium Laureth 13-Carboxylate (*Sandopan LS-24N) | 0.3 |
| Sodium Lauroamphoacetate (*Genagen LAA) | 0.87 |
| Perfume | qs |
| Preserver | qs |
| Water | qs |
| NaCl | qs |

EXAMPLE 2

Shampoo Formulation

| | |
|---|---|
| Alpha Olefin Sulfonate (Hostapur OS) | 7.0 |
| Sodium Lauryl Ether Sulfate (*Genapol LRO) | 3.0 |
| Sodium Lauroamphoacetate (*Genagen LAA) | 4.0 |
| Alkyl Dimethyl Hydroxy Ethyl Ammonium Chloride (*Praepagen HY) | 0.5 |
| Perfume | qs |
| Preserver | qs |
| Water | qs |
| NaCl | qs |

(*) commercialized by Clariant SA

What is claimed is:

1. A method for the treatment of hair, comprising contacting the hair with a treatment composition comprising:
   a) from 2% to 70% by weight of at least one anionic surfactant,
   b) from 0.05% to 10% by weight of at least one $C_8$–$C_{22}$ alkyldimethylhydroxyethyl -ammonium chloride and
   c) optionally from 0.1% to 15% by weight of one or more nonionic or amphoteric surfactants or a mixture thereof, with the proviso that the surfactants used as component c) are not selected from the group consisting of silicone compounds.

2. The method of claim 1, wherein the hair treatment composition comprises from 2% to 50% by weight of anionic surfactants and from 0.5% to 8.0% by weight of alkyl dimethylhydroxyethyl-ammonium chloride.

3. The method of claim 1 wherein the anionic surfactant is selected from the group consisting of alkyl sulfates, alkyl ether sulfates, secondary alkane sulfonates, alpha olefin sulfonates, acyl isocyanates, linear alkylbenzene sulfonates, isethionates and mixtures thereof.

4. The method of claim 1 wherein component c is selected from the group consisting of alkyl polyalkylene glycols, alkylaryl polyalkylene glycols, alkyldimethyl amine oxides, dialkyl methyl amine oxides, alkylamidopropyl amine oxides, alkyl glucamides, alkyl polyglycosides, oxalkylated fatty acids, oxalkylated fatty acid esters, alkyl amines, alkyl amidopropyl betaines, alkyl dimethyl betaines, alkyl amphoacetates or -diacetates, and mixtures thereof.

5. The method of claim 1, wherein the amphoteric surfactants are selected from the group consisting of cocamidopropyl betaine, sodium lauroamphoacetate, disodium lauroam phodiacetate, and mixtures thereof.

6. The method of claim 1, wherein the hair treatment composition further comprises an additional component selected from the group consisting of oils, emulsifiers, thickeners, natural and synthetic polymers, stabilizers, waxes, solubilizers, fillers, acids, bases, buffers, biological active compounds, vitamins natural extracts, UV-absorber, perfumes, perfume carriers, pearlescing agents, dyes, bleaching agents, other ingredients conventionally used in cosmetic compositions, and mixtures thereof.

7. The method of claim 1, wherein the treatment composition is a shampoo.

8. The method of claim 1, wherein the treatment composition is a shampoo for African-ethnic hair.

\* \* \* \* \*